United States Patent [19]

Wallace

[11] Patent Number: 5,078,694
[45] Date of Patent: Jan. 7, 1992

[54] PROTECTIVE SHIELD FOR IV DEVICE
[75] Inventor: Henry G. Wallace, Colchester, United Kingdom
[73] Assignee: H. G. Wallace, Ltd., Colchester, United Kingdom
[21] Appl. No.: 321,176
[22] Filed: Mar. 9, 1989
[30] Foreign Application Priority Data Apr. 12, 1988 [GB] United Kingdom ............... 8808571

[51] Int. Cl.$^5$ ............................................. A61M 5/32
[52] U.S. Cl. ................................... 604/192; 604/201; 604/263; 604/283; 604/905
[58] Field of Search ............... 604/192, 263, 162, 171, 604/280, 244, 175, 283, 905, 88, 200–201, 413, 415

[56] References Cited

U.S. PATENT DOCUMENTS

| 3,574,306 | 4/1971 | Alden | 604/162 |
|---|---|---|---|
| 4,445,893 | 5/1984 | Bodicky | 604/165 |
| 4,445,896 | 5/1984 | Giantorco | 604/88 |
| 4,573,975 | 3/1986 | Frist et al. | 604/192 |
| 4,632,673 | 12/1986 | Tiitola et al. | 604/415 |
| 4,673,394 | 6/1987 | Fenton, Jr. et al. | 604/175 |
| 4,840,613 | 6/1989 | Balbierz | 604/171 |
| 4,880,413 | 11/1989 | Giuffre et al. | 604/263 |
| 4,889,256 | 12/1989 | Fowles | 604/415 |

FOREIGN PATENT DOCUMENTS 2178664  2/1987  United Kingdom ............... 604/905

OTHER PUBLICATIONS

CompGard TM, Comp Equipment Corporation Brochure.

Primary Examiner—Stephen C. Pellegrino
Assistant Examiner—Michael Rafa
Attorney, Agent, or Firm—Laubscher, Presta & Laubscher

[57] ABSTRACT

The invention provides an assembly of a protective shield for a needle channel and a self-sealing diaphragm, wherein the protective shield is generally cup-shaped and is provided with an aperture, said self-sealing diaphragm being retained in the aperture, the arrangement being such as to protect the fingers of the operative from needle-stick by the miss-direction of a hypodermic needle. The diameter of the aperture may approximate to, or be smaller than, the internal diameter of the inlet of the needle channel so that only is needle-stick obviated, but also the tendency of the needle point to tear the seal-sealing diaphragm is significantly reduced.

10 Claims, 1 Drawing Sheet

PROTECTIVE SHIELD FOR IV DEVICE

BACKGROUND OF THE INVENTION

The present invention relates to a protective shield for an IV device, particularly a device incorporating a resealable diaphragm.

Protective shields for hypodermic needles are known per se. For example, EP-A-192453 and WO 85/03006 each disclose a needleshield for use with a tubular cover for a needle assembly having an opening at one end to receive a disposable hypodermic needle so that the hub of the needle is locked into the cover. The needle shield is a sliding co-operative fit, or is integral, with the external peripheral surface of the cover so that in one position it protects the hand of an operative from needle-stick and in another it allows the cover to slide through the aperture in the shield to allow the safe disposal of the cover and needle assembly.

Similarly, U.S. Pat. No. 4,573,975 relates to a protective shield surrounding a container for a hypodermic needle, said protective shield being foldable down against the body of the container in the pre-use condition. Withdrawal of the needle from the container allows the shield to expand to provide a protective shield, which shield remains expanded to allow the needle to be safely re-inserted in the container for safe disposal.

In the foregoing cases the needle and needle hub assembly are positioned for disposal in the tubular cover with the needle hub in sliding inter-engagement with the tubular cover to retain the same for safe disposal. The entrance to the needle cover is never obturated when the needle has been removed therefrom. Needle-stick is also a problem with intermittent injection devices using a self-sealing diaphragm. This is particularly so since the diaphragms of said devices often provide a relatively small target, and because it is usual to hold the device between the fingers while inserting the needle into the diaphragm. The material of the diaphragm, oversailing the mouth of the inlet, tends to retain the needle point and guide it towards the fingers.

SUMMARY OF THE INVENTION

In a first aspect of the invention, therefore, there is provided an assembly of a protective needle shield and a self-sealing diaphragm, characterised in that the shield is generally cup-shaped and is provided with an aperture, said self-sealing diaphragm being retained in the aperture.

It will be appreciated that in contra-distinction to the arrangements of the prior art, the arrangement of the present invention provides an inlet to a catheter which is obturated by the diaphragm and shield assembly at all times.

Catheter and diaphragm assemblies have heretofore been formed by positioning a resilient self-sealing member over an inlet to the catheter or circuit.

A difficulty with arrangements of this type is that the inlet has a relatively significant thickness and if, in use, the hypodermic needle is not centrally positioned over the aperture of the inlet, the needle tip tends to contact the harder material of the inlet per se. This can lead to indirect needle-stick because the needle can slide down between the outer surface of the mouth-piece and the outer annular surface of the diaphragm to pierce the fingers of the operative.

Further in poor light, for example, it is easy to miss the diaphragm with the needle and to press the needle into the fingers.

Additionally, the reaction of the operative if the needle tip hits the edges of the inlet is to increase axial pressure and to alter the angle of the needle. This can result in the needle entering the inlet at a relatively acute angle which, when corrected by the operative, or by contact of the angled needle shaft with the interior of the inlet, results in the diaphragm being torn by lateral movement of the needle shaft.

Thus, the diaphragm can become open to the atmosphere when the needle is then withdrawn, encouraging incidental infection.

In a second aspect of the invention, therefore, there is provided an assembly as just described wherein the diameter of the aperture of a cup-shaped protective needle shield approximates to, or is smaller than the internal diameter of the inlet of the catheter with which it is assembled.

This ensures that if the hypodermic needle approaches the aperture at an acute angle, or if the needle slides off the shield into the diaphragm, it will pierce rather than tear the diaphragm.

The assemblies of the invention may be produced with an internal or external diaphragm.

The external diaphragm is adapted for circumstances where it is clinically desirable to be able to remove the diaphragm at will from the inlet. In such circumstances the diaphragm is retained on the inlet by its own resilience, and may be removed by manipulation by the operative. Unfortunately it is possible to inadvertently remove the diaphragm, especially because assemblies of this type tend to be used by patients with indwelling catheters who are mobile.

It has been found that this may theoretically be overcome by positioning a collar on the inlet and diaphragm assembly. However, assemblies with such a collar make it difficult to remove the diaphragm when clinically desirable.

The protective shield of the present invention are preferably formed with a downwardly dependent slightly convergent tubular portion to locate the external portion of the diaphragm upon the inlet. The radially extending portion of the guard makes it possible to readily apply sufficient axial pressure to remove the shield from the inlet and hence ensure that the diaphragm can be readily removed when clinically desired. The reverse process may also be readily effected because the protective shield is more readily manipulated than a collar, and because radially inwardly applied pressure to the periphery of the shield tends to relieve the resilient pressure applied by the convergent tubular portion, and hence assist manipulation.

The assemblies of the invention also comprehend the use of internal diaphragms. These may be of the Luer-Lock type and comprise a generally tubular housing having at one end a Luer-Lock assembly of known type, and at the other end an internal diaphragm retained by an upstanding annular rib. The internal diaphragms of this type are not designed to be removed in use.

This type of assembly tends to increase the chances of needle-stick. This is because the annular rib, if missed by the needle, tends to guide the needle tip into the fingers of the operative. The arrangement of the present invention not only improves significantly on assemblies of the prior art type because needle-stick is avoided, but also simplify assembly because the needle guards are used to retain the internal diaphragm in the Luer-Lock hub by virtue of the fact that the aperture of the needle protective shield is of a diameter smaller than the periphery of the diaphragm material.

In assemblies of the invention it is most desirable that the diaphragm which is disposed across the inlet is at least substantially contiguous with the curve of the protective shield so that the diaphragm and shield may be readily swabbed prior to use.

The shields of the present invention may also be provided with an inturned anti-slip bead adjacent the upper rim thereof.

BRIEF DESCRIPTION OF THE DRAWINGS

The invention will now be described, by way of illustration only, with reference to the accompanying drawings wherein.

DESCRIPTION OF THE PREFERRED EMBODIMENTS

Figure 1:
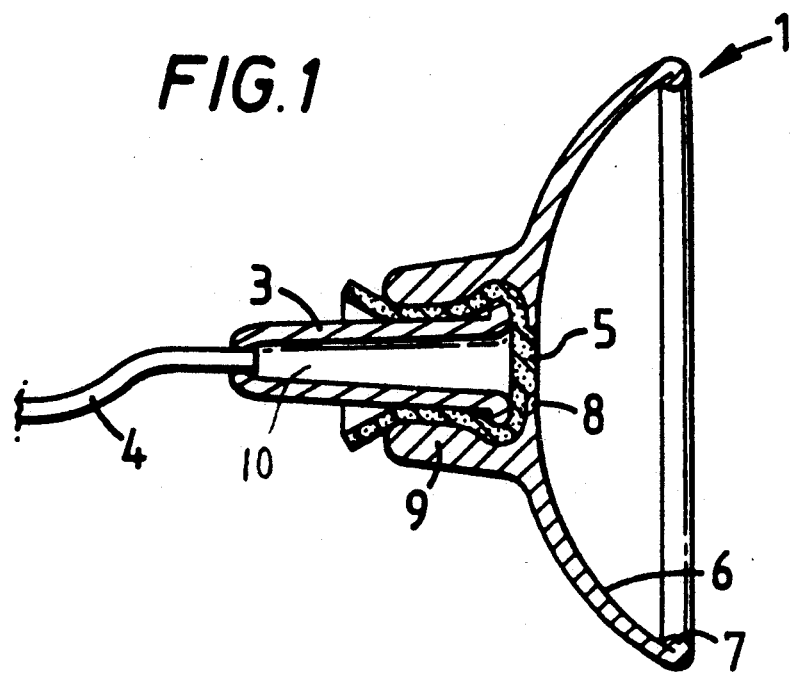
FIG. 1 shows a transverse cross section through an assembly in accordance with the present invention showing a detachable diaphragm and FIG. 2 shows a transverse cross section through an assembly in accordance with the present invention showing a Luer-Lock assembly comprising an internal diaphragm.

With reference to FIG. 1 a detachable protective shield 1 is formed upon a generally tapered inlet 3. The inlet 3 is connected at its remote end to a catheter tube 4 which may, for example, be attached to an indwelling catheter disposed in a patient. The inlet 3 is formed with a hollow portion forming a needle channel 10.

The inlet 3 opens at its end remote from the catheter tube 4 onto a diaphragm 5 formed of a resilient natural rubber or a self-sealing elastomer. The resilient material of the diaphragm 5 is self-sealing when pierced by a hypodermic syringe. The diaphragm 5 has a configuration such that it extends down the external portions of the inlet 3. In an alternative embodiment the diaphragm 5 also extends down the internal surfaces of the inlet 3 thereby providing a double seal thereupon.

Concave needle shield 6 in accordance with the present invention is formed by a cup-shaped member having an inturned annular rib 7 adjacent its uppermost and outermost periphery. The concave shield 6 is formed preferably of a hard plastics material which cannot ordinarily be pierced by a hypodermic needle. The cup-shaped shield 6 is generally concave and terminates towards its central portion in an aperture 8.

Downwardly depending from the convex surface of the shield 6 is an annular hollow frusto-conical clip portion 9. It will be noted that the aperture 8 is of a size approximating to the internal diameter of the inlet 3.

In use, the diaphragm 5 is positioned over the inlet 3 in accordance with prior art practice. The annular clip portion 9 of the shield 6 is then urged axially of the inlet 3 thereby clipping the diaphragm 5 onto the external surface of the inlet 3. The aperture 8 has a portion immediately adjacent thereto which is comparatively thin. The material forming the self-sealing diaphragm 5 is comparatively soft. It will be seen that axial pressure applied to the shield 6 relative to the inlet 3 interengages the edges of the aperture 8 against the diaphragm 5 such that diaphragm 5 is slightly deformed against the harder material of the protective shield 6 so that in its 'in use' position the diaphragm 5 and the upper peripheral edge of the shield 6 are substantially contiguous, thereby they may be readily swabbed.

It will be observed that the shield 6 may be readily withdrawn from the inlet 3 if it is desired to remove the diaphragm 5 merely by applying a reasonable amount of axial pressure. This allows not only the diaphragm to be removed if it is clinically desirable to do so, but also for damaged diaphragms to be readily replaced.

Further, it will be appreciated that if a hypodermic needle strikes the concave surface of the shield 6 and slides down onto the diaphragm 5 it will pass through the diaphragm 5 without a tearing motion being engendered.

Figure 2:
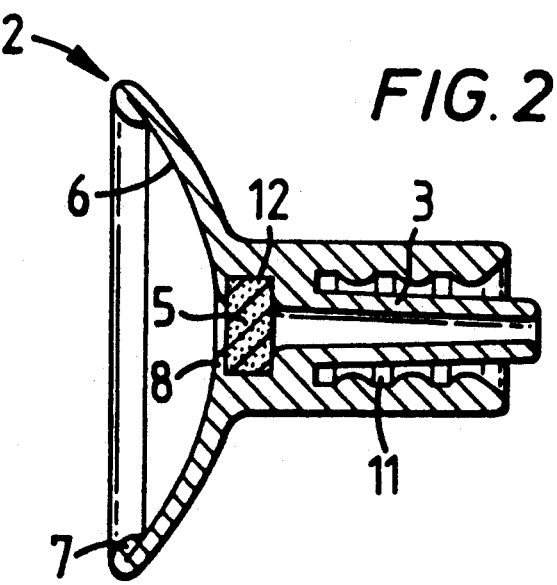

The arrangement of FIG. 2 differs from the arrangement of FIG. 1 in that instead of the inlet 3 there is provided a Luer-Lock assembly of known type. This type of assembly 2 comprises a diaphragm 5 which is in the form of an annular block as shown in FIG. 2. The inlet 3 is formed of a generally tubular member having a Luer-Lock assembly to its interior in accordance with well known prior art practice. The shield 6 is separately formed from the Luer-Lock inlet 3 and is of the general configuration as described in FIG. 1.

The inlet 3 of FIG. 2 comprises a recess to retain the annular block of diaphragm material 5. The shield 6 is formed with an aperture and is identical on the operative surface with that of FIG. 1. However, to its convex side a recess 12 is formed in order to accommodate the end of the inlet 3. The recess locates the end of the inlet 3 relative to the convex surface of the shield 6 and may be located thereupon by means of a suitable adhesive, or by suitable moulded interlocking annular rib means. The assembly of the arrangement of FIG. 2 is much simplified in that it is only necessary to position the diaphragm material 5 in the recess provided, and to locate the recess in the convex surface of the shield upon the inlet 3 appropriately. The aperture 8 is sized so that tearing of the diaphragm is avoided.

In a further form of the invention the needle shield 6 may be formed of a malleable material, especially a mouldable malleable material such as High Density Polyethylene. This enables the shield 6 to be squeezed to a shape which provides the maximum convenience in use.

It has thus been found that the arrangements of the present invention not only provide adequate protection for operatives utilising a hypodermic needle to pierce a self-sealing diaphragm in an indwelling catheter assembly for example, but also assists in the manufacture and utilisation of such assemblies.

The invention provides, therefore, protective shields as just described, assemblies of such shields with self-sealing diaphragms, and catheter assemblies utilising the same.

I claim:

1. A protective shield assembly for a needle channel comprising a protective shield and a self-sealing diaphragm, wherein the protective shield is generally cup-shaped and is adapted to extend generally radially of the diaphragm to protect the fingers from needle stick, and is provided with an aperture, said self-sealing diaphragm being retained in use in the aperture;

wherein the diameter of the aperture approximates to or is smaller than, the internal diameter of the inlet of the needle channel with which it is adapted to be used;

and wherein the protective shield is formed of a malleable, non-resilient material to allow the shield to be manually formed to and retained in a shape configured to a body surface.

2. An assembly according to claim 1 characterised in that the diaphragm is externally disposed about the needle channel and in that the protective shield is provided with a convergent tubular portion adapted to be a push-fit over the external diaphragm and the needle channel.

3. An assembly according to claim 2 characterised in that the diaphragm is substantially contiguous with the curve of the shield.

4. An assembly according to claim 1 characterised in that the diaphragm is internally retained at the entrance to the needle channel by a portion of the protective shield adjacent the aperture.

5. An assembly according to claim 1 characterised in that the protective shield is provided at its outermost rim with an inturned rib.

6. A protective shield assembly for a needle channel comprising a protective shield and a self-sealing diaphragm, wherein the protective shield is generally cup-shaped and is adapted to extend generally radially of the diaphragm to protect the fingers from needle stick, and is provided with an aperture, said self-sealing diaphragm being retained in use in the aperture;

wherein the diameter of the aperture approximates to or is smaller than, the internal diameter of the inlet of the needle channel with which it is adapted to be used, and wherein the diaphragm is externally disposed about the needle channel and the protective shield is provided with a tubular portion adapted to be a resilient push fit over the external diaphragm when positioned about the needle channel.

7. An assembly according to claim 6 characterised in that the protective shield is formed of a malleable material.

8. An assembly according to claim 6 characterized in that the diaphragm is internally retained at the entrance to the needle channel by a portion of the protective shield adjacent the aperture.

9. An assembly according to claim 6 characterised in that the diaphragm is substantially contiguous with the curve of the shield.

10. An assembly according to claim 6 characterized in that the protective shield is provided at its outermost rim with an inturned rib.

* * * * *